United States Patent
Abe et al.

(10) Patent No.: US 6,849,432 B2
(45) Date of Patent: Feb. 1, 2005

(54) PROCESS FOR PRODUCING AMIDE COMPOUNDS

(75) Inventors: Takeya Abe, Chiba (JP); Kiyoshi Ito, Chiba (JP); Kenju Sasaki, Chiba (JP); Seiichi Watanabe, Chiba (JP); Toshihisa Tachibana, Chiba (JP); Tamotsu Asano, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 560 days.

(21) Appl. No.: 09/980,102

(22) PCT Filed: Mar. 23, 2001

(86) PCT No.: PCT/JP01/02333

§ 371 (c)(1),
(2), (4) Date: Nov. 29, 2001

(87) PCT Pub. No.: WO01/73101

PCT Pub. Date: Oct. 4, 2001

(65) Prior Publication Data

US 2002/0160466 A1 Oct. 31, 2002

(30) Foreign Application Priority Data

Mar. 29, 2000 (JP) .......................... 2000-91203

(51) Int. Cl.⁷ ............................ C12P 13/02; C12N 9/88
(52) U.S. Cl. ........................ 435/129; 435/227; 435/228; 435/232
(58) Field of Search ................................ 435/129, 232, 435/227, 228

(56) References Cited

U.S. PATENT DOCUMENTS

| 4,248,968 A | | 2/1981 | Watanabe et al. |
| 4,440,858 A | | 4/1984 | Yamaguchi et al. |
| 4,524,077 A | * | 6/1985 | Ruest et al. ................. 514/557 |
| 5,648,256 A | * | 7/1997 | Yamada et al. ............. 435/232 |
| 6,153,415 A | * | 11/2000 | Oriel et al. .................. 435/129 |

FOREIGN PATENT DOCUMENTS

| EP | 0 790 310 A2 | 8/1997 |
| EP | 0 943 686 A2 | 9/1999 |
| JP | 11-89575 | 4/1999 |

OTHER PUBLICATIONS

Cheo Young et al., "Continuous Production of Acrylamide Using Immobilized Brevibacterium sp. CH2 in a Two–Stage Packed Bed Reactor", Biotechnol. Lett., vol. 12, No. 1, pp. 23–28, 1990.

* cited by examiner

Primary Examiner—Herbert J. Lilling
(74) Attorney, Agent, or Firm—Burns, Doane, Swecker & Mathis, LLP

(57) ABSTRACT

The invention is a process for continuously producing an amide compound by reacting a microorganism fungus body containing nitrile hydratase or a processed product of the microorganism fungus body with a nitrile compound in an aqueous medium, characterized in that after contacting said fungus body or said processed product of said fungus body with said nitrile compound in said aqueous medium, a reaction solution thus obtained is further subjected to reaction under conditions having a plug flow region, and according to the invention, an amide compound aqueous solution of a high concentration a high purity can be easily obtained in an extremely high conversion rate of a nitrile compound without a condensation process.

4 Claims, No Drawings

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Oligonucleotide for PCR primer

<400> SEQUENCE: 1
aacatcatgc gcaagtcg                                              18

<210> SEQ ID NO 2
<211> LENGTH: 17
<212> TYPE: DNA
<213> ORGANISM: Artificial Sequence
<220> FEATURE:
<223> OTHER INFORMATION: Oligonucleotide for PCR primer

<400> SEQUENCE: 2
caggaaacag ctatgac                                               17

<210> SEQ ID NO 3
<211> LENGTH: 20
<212> TYPE: DNA

-continued

```
<213> ORGANISM: Artificial Sequence
<220> FEATURE:
<223> OTHER INFORMATION: Oligonucleotide for PCR primer

<400> SEQUENCE: 3
ggccagtgcc tagcttacat                                               20

<210> SEQ ID NO 4
<211> LENGTH: 17
<212> TYPE: DNA
<213> ORGANISM: Artificial Sequence
<220> FEATURE:
<223> OTHER INFORMATION: Oligonucleotide for PCR primer

<400> SEQUENCE: 4
gttttcccag tcacgac                                                  17

<210> SEQ ID NO 5
<211> LENGTH: 18
<212> TYPE: DNA
<213> ORGANISM: Artificial Sequence
<220> FEATURE:
<223> OTHER INFORMATION: Oligonucleotide for PCR primer

<400> SEQUENCE: 5
aactggtaca aggagccg                                                 18

<210> SEQ ID NO 6
<211> LENGTH: 18
<212> TYPE: DNA
<213> ORGANISM: Artificial Sequence
<220> FEATURE:
<223> OTHER INFORMATION: Oligonucleotide for PCR primer

<400> SEQUENCE: 6
ccgaactaca gcgtctac                                                 18
```

PROCESS FOR PRODUCING AMIDE COMPOUNDS

TECHNICAL FIELD

The present invention relates to a process for producing an amide compound, and more particularly, it relates to a process for continuously producing an amide compound aqueous solution of a high concentration by hydrating a nitrile compound at a high conversion rate, in which the amount of the residual nitrile compound after the reaction is small, and the process is suitable for industries.

BACKGROUND ART

The hydration process using a nitrile compound as a raw material is used as one of the major processes for producing an amide compound, and it is known that in particular, acrylamide is produced from acrylonitrile as a raw material with ametallic copper catalyst, such as a Raney copper, and in recent years, with a hydration catalyst, such as a microorganism fungus body containing nitrile hydratase or a processed product of the microorganism fungus body.

In the foregoing process, a product, acrylamide, is generally supplied in the form of an aqueous solution or crystals, and upon using the same, it is generally used after diluting or dissolving with an aqueous solvent. Therefore, particularly in recent years, it is almost supplied in the form of an aqueous solution.

Upon supplying an acrylamide aqueous solution, those having a high concentration is demanded as a product form from the standpoint of the cost for transportation, storage and the like, but it is necessary that deposition of crystals is prevented during transportation, storage and the like. Therefore, the concentration of acrylamide that is suitable for transportation, storage or the like near ordinary temperature is generally about from 40 to 50% by weight.

However, the concentration of acrylamide in the reaction process in the conventional industrial production technique is generally less than 40% by weight while depending on the production process and the species of the catalyst used. This is because, in the case where the concentration of acrylonitrile and/or acrylamide in the reaction process is increased, there are such tendencies that the catalyst activity is lost, the reaction becomes incomplete to leave acrylonitrile as a raw material, the amounts of by-products are increased, and the like phenomenon, and such a problem occurs as restriction due to removing capability of reaction heat, whereby it is generally difficult that a final product having a product concentration of acrylamide is directly obtained when the foregoing reaction is completed.

Therefore, in the current industrial production process of acrylamide, the concentration of acrylamide is restricted, or the conversion rate of acrylonitrile as a raw material is suppressed to a low level by a method of supplying acrylonitrile as a raw material in a multistage manner (JP-B-57-1234), a raw material diluting method by circulating part of the reaction solution (JP-B-58-35077), and the like, whereby the concentration of acrylamide in the reaction solution is kept to less than 40% by weight to suppress the inactivation of the catalyst and the increase of the amount of by-products. Therefore, it is general that condensation is carried out to increase the concentration of the resulting acrylamide aqueous solution and/or to remove the remaining acrylonitrile.

While the condensation of the acrylamide-containing solution is generally carried out under reduced pressure, however, there is a danger of polymerization during condensation because acrylamide is a polymerizable monomer having an extremely high reactivity. Accordingly, such measures are carried out as a method of stabilization by introducing oxygen upon condensation, a method of co-existing nitrogen monoxide, a method of co-existing a metallic ion, and the like, but it is difficult that the polymerization is completely prevented.

JP-A-11-89575 discloses a production process of acrylamide by utilizing a microorganism fungus body or a processed product of the fungus body, in which acrylonitrile as a raw material is added in such a manner that the concentration of acrylonitrile at the start of the reaction or during the reaction is more than the saturated concentration of acrylonitrile in an aqueous medium, whereby a high acrylamide concentration can be obtained by a small amount of the fungus body. Although an acrylamide aqueous solution having a concentration of 40% by weight or more can be obtained without condensation, there are some cases where problems occur depending on the relationship between the used amount of the catalyst for the reaction or the reaction temperature and the concentration of acrylonitrile at the start of the reaction or during the reaction. For example, in the case where the reaction is completed in a short period of time, the heat of reaction in the initial stage is large to require a relatively large heat exchanger with respect to the reactor, and in the case where the conversion rate of acrylonitrile is 99% or more, on the other hand, a long reaction time is required.

Under the foregoing circumstances, such an industrial production process of an amide compound is demanded that the conversion rate of a nitrile compound is high, the condensation process is unnecessary, and an amide compound can be effectively obtained in a high concentration.

DISCLOSURE OF THE INVENTION

The invention has been developed to solve the foregoing problems, and an object thereof is to provide a process for producing an amide compound in a high concentration by conversing a nitrile compound at a high conversion rate, in which an amount of a residual nitrile compound is extremely small, the process can be continuously operated, and the process is suitable for industrial production.

As a result of earnest investigations by the inventors to attain the object, it has been found that it is an effective measure to attain the object that a microorganism fungus body containing nitrile hydratase or a processed product of the microorganism fungus body is made in contact with a nitrile compound in an aqueous medium to exert reaction, and then the reaction solution is further subjected to reaction under conditions having a plug flow region.

That is, the invention is (1) A process for continuously producing an amide compound by reacting a microorganism fungus body containing nitrile hydratase or a processed product of the microorganism fungus body with a nitrile compound in an aqueous medium, characterized in that after contacting the fungus body or the processed product of the fungus body with the nitrile compound in the aqueous medium, a reaction solution thus obtained is further subjected to reaction under conditions having a plug flow region;

(2) A production process as described in the item (1), wherein the nitrile compound is acrylonitrile, and a ratio of water and acrylonitrile upon contacting with the fungus body or the processed product of the fungus body is from 0.4 to 1.5 parts by weight of acrylonitrile per 1.0 part by weight of water; and (3) A production process as described in the item (1) or (2), wherein the microorganism fungus body is a transformant obtained by expressing a nitrile hydratase gene cloned from the microorganism in an arbitrary host.

BEST MODE FOR CARRYING OUT THE INVENTION

What is important in the invention is that the microorganism fungus body containing nitrile hydratase or the processed product of the microorganism fungus body is used as an amidation catalyst for amidation of a nitrile group in a nitrile compound, and an amide compound aqueous solution having a high concentration is effectively produced with a high conversion rate while the production of by-products is suppressed.

The nitrile hydratase referred in the invention is an enzyme having capability of hydrolyzing a nitrile compound to produce a corresponding amide compound.

The microorganism containing nitrile hydratase is not particularly limited as far as it produces nitrile hydratase having capability of hydrolyzing a nitrile compound to produce a corresponding amide compound, and it maintains an activity as nitrile hydratase in a 30% by weight aqueous solution of acrylamide. Specifically, preferred examples thereof include microorganisms belonging to Nocardia, Corynebacterium, Bacillus, thermophilic Bacillus, Pseudomonas, Micrococcus, Rhodecoccus represented by rhodochrous, Acinetobacter, Xanthobacter, Streptomyces, Rhizobium, Klebsiella, Enterobacter, Erwinia, Aeromonas, Citrobacter, Achromobacter, Agrobacterium, and Pseudonocardia represented by thermophilia.

A transformant obtained by expressing a nitrile hydratase gene cloned from the microorganism in an arbitrary host is also included in the microorganism of the invention. While *Escherichia coli* can be exemplified as described later as a representative example of the arbitrary host referred herein, it is not particularly limited to *Escherichia coli*, but Bacillus, such as *Bacillus subtilis* and the like, and other microorganism strains, such as yeast, actinomycete and the like, are also included. Examples thereof include MT-10822 (the strain has been deposited in National Institute of Bioscience and Human Technology, Ministry of International Trade and Industry, 1-3, Higashi 1-chome, Tsukuba-shi, Ibaraki-ken, on Feb. 7, 1996 under Receipt No. FERMBP-5785 based on the Budapest Treaty and Regulations on the International Recognition of the Deposit of Microorganisms for the Purposes of Patent Procedure). The microorganism of the invention also includes a transformant obtained by expressing a mutant nitrile hydratase that has been further improved in amide compound resistance, nitrile compound resistance and temperature resistance by displacing, deleting, canceling or inserting one of or two or more of constitutional amino acids of the enzyme with other amino acids by using DNA splicing technique.

Upon producing an amide compound by using the foregoing microorganisms, a fungus body or a processed product of a fungus body is generally used. The fungus body can be prepared by utilizing an ordinary method having been known in the fields of molecular biology, bioengineering and genetic engineering. For example, such a method can be exemplified that after the microorganism is planted in an ordinary liquid culture medium, such as an LB medium, an M9 medium and the like, it is grown at an appropriate culture temperature (which is generally from 20 to 50° C., and 50° C. or higher is possible for thermophile), and then the microorganism is separated and recovered from the culture liquid by centrifugal separation.

The processed product of the microorganism fungus body in the invention denotes an extract and a trituration product of the microorganism fungus body, a post-separated product obtained by separating and purifying a nitrile hydratase active fraction of the extract and the trituration product, and a fixed product obtained by fixing the microorganism fungus body, or the extract, the trituration product or the post-separated product of the fungus body with an appropriate carrier, and these are included in the processed product of the fungus body of the invention as far as they has an activity as nitrile hydratase. These may be used solely as a single species, or in alternative, two or more species thereof may be used simultaneously or alternately.

The mode of reaction when an amide compound is obtained from a nitrile compound by using the microorganism fungus body containing nitrile hydratase or the processed product of the microorganism fungus body in the invention may be carried out by using two or more reactors, and the microorganism fungus body or the processed product of the fungus body, the nitrile compound and the aqueous medium are supplied to the preceding reactor. At this time, the mode of reaction is not particularly limited and may be either a suspended bed or a fixed bed, and in general, a suspended bed in a vessel type reactor equipped with an agitator is preferably used because of easiness of removing reaction heat.

In the invention, the kind of the nitrile compound is not particularly limited, and specific examples thereof include nitrile compounds having about from 2 to 20 carbon atoms, which encompass a wide range of nitrites, such as an aliphaticnitrile, an aromatic nitrile and the like. Examples of the aliphatic nitrile include a saturated or unsaturated nitrile having from 2 to 6 carbon atoms, for example, an aliphatic saturated mononitrile, such as acetonitrile, propionitrile, butyronitrile, isobutyronitrile, valeronitrile, isovaleronitrile, capronitrile and the like; an aliphatic saturated dinitrile, such as malononitrile, succinonitrile, adiponitrile and the like; an aliphatic unsaturated nitrile, such as acrylonitrile, methacrylonitrile, crotononitrile and the like. Examples of the aromatic nitrile include benzonitrile, o-, m- or p-chlorobenzonitrile, o-, m- or p-fluorobenzonitrile, o-, m- or p-nitrobenzonitrile, o-, m- or p-tolunitrile, benzyl cyanide. Preferred examples among these include acrylonitrile, methacrylonitrile, crotonoitrile and the like.

The aqueous medium in the invention includes water and an aqueous solution having dissolved therein a buffer agent, such as a phosphate and the like, an inorganic salt, such as a sulfate, a carbonate and the like, a hydroxide of an alkali metal, an amide compound or the like in an appropriate concentration.

In the invention, the concentration of the nitrile compound supplied to the preceding reactor is such a concentration that is larger than the saturated concentration of the nitrile compound at the start of the reaction. The upper limit of the concentration is not particularly limited, but an overly excessive amount of the nitrile compound supplied brings about necessity of a large amount of a catalyst and a reactor having a too large volume for completing the reaction, and a too large heat exchanger for removing heat, which cause increase of the economical cost of the equipments. Therefore, the supplied concentration of the nitrile compound is preferably such a concentration that when the entire nitrile compound is converted to the corresponding amide compound, the theoretical concentration of the solution thus produced is from 40 to 80% by weight in the case of acrylamide, more specifically, the amount of acrylonitrile is preferably from 0.4 to 1.5 parts by weight per 1.0 part of water. In the case of methacrylamide, the nitrile compound and water are preferably supplied in such a concentration that the theoretical concentration of the solution thus produced is from 10 to 40% by weight, more specifically, the amount of methacrylonitrile is preferably from 0.08 to 0.5 part by weight per 1.0 part of water.

In the invention, the reaction solution withdrawn from the preceding reactor is further subjected to reaction under conditions having a plug flow region. More specifically, the reaction solution withdrawn from the preceding reactor is supplied to a subsequent reactor having a plug flow region. The reactor having a plug flow region referred herein is generally a reactor that sometimes referred to as a tubular reactor, in which a reaction proceeds while a reaction solution is moved in a piston flow inside a tube having a piping configuration, and those having a double pipe form and a shell and tube form can be used for removing the reaction heat.

However, the reactor having a plug flow region in the invention is not limited to the foregoing forms, but reactors of other forms can be satisfactorily used as far as they have such a configuration that a short pass of the reaction solution is difficult to occur. That is, those having such a structure can be used as the reactor having a plug flow region that the reaction solution can have a plug flow region depending on the conditions, such as a flow rate and the like, and the reaction heat can be removed. For example, various structures can be employed, such as a spiral form or a plate form in a heat exchanger, a tower reactor and the like. Furthermore, even in the case where a baffle plate or a packing is provided inside a reactor for uniforming the flow conditions of the reaction solution, it can be used as the reactor having a plug flow region as far as it has a plug flow region of the reaction solution depending on the conditions, such as a flow rate and the like.

The preceding reactor and the subsequent reactor having a plug flow region as described in the foregoing each is not limited to one reactor, but they each may be a single reactor or plural reactors arranged serial or parallel. The reaction times (retention times) of the reactions in the preceding and subsequent reactors are not constant since they depend on the conditions, such as the amount of the catalyst used, the temperature and the like, and in general, each of them is in a range of from 0.5 to 40 hours, and preferably in a range of from 1 to 20 hours. The reaction time in the preceding reactor is from 20 to 99%, and preferably from 40 to 90%, of the total reaction time, and the reaction time in the subsequent reactor is from 1 to 80%, and preferably from 10 to 60%, of the total reaction time.

The amount of the catalyst used varies depending on the reaction conditions and the species and the forms of the catalyst, and in general, it is from 10 to 50,000 ppm by weight, and preferably from 50 to 30,000 ppm by weight, based on the reaction solution in terms of a dried weight of the microorganism fungus body.

The amidation reaction is generally carried out under ordinary pressure or pressure near ordinary pressure, and it may be carried out under increased pressure in order to increase the solubility of the nitrile compound in the aqueous medium. The reaction temperature is not particularly limited as far as it is the freezing point of the aqueous medium or higher, and it is preferably carried out in the range of from 0 to 50° C., and more preferably from 10 to 40° C. The reaction is also carried out in a slurry state in which products are crystallized in the reaction solution.

The pH of the reaction solution on the amidation reaction is not particularly limited as far as the activity of the nitrile hydratase is maintained, and it is preferably in a range of from pH 6 to 10, and more preferably in a range of from pH 7 to 9.

In the example, the acquisition of an amino acid substituted body maintaining the nitrile hydratase activity is carried out by site-specific mutation. However, the similar results as the example can be obtained by such a manner that a spliced plasmid is obtained by other methods than the site-specific mutation based on the mutation point and the species of the substituted bases disclosed in the example, and is then introduced into the host cell.

For example, a DNA fragment having such a base sequence that the base sequence of the DNA in the region corresponding to the mutation point disclosed in the example is the sequence after substitution of amino acids is synthesized by a DNA synthesizer or the like, and the resulting fragment and the region of the pPT-DB1 having been separated corresponding to the fragment are substituted by each other, whereby the objective spliced plasmid can be obtained.

EXAMPLE

The invention will be described in more detail below with reference to the examples, but the invention is not construed as being limited to the examples. In the following, HPLC analysis of a reaction solution is carried out by using ULTRON 80HG (50 mm×8 mm in diameter) as a column and a 10 mM phosphoric acid aqueous solution as a developer, and acrylamide and acrylonitrile are detected by optical absorbance at 220 nm to measure the concentrations.

Example 1

(1) Acquisition of Amino Acid Substituted Body maintaining Nitrile Hydratase Activity In order to substitute the sixth Leu on the α subunit by Met, the site-specific mutational introduction was carried out by using "LA PCR in vitro mutagenesis Kit" produced by Takara Shuzo Co., Ltd. using the pPT-DB1 plasmid DNA obtained according to JP-A-9-275978 as a template. Hereinafter, the "LA PCR in vitro mutagenesis Kit" will be simply referred to as a kit. The following examples basically followed the principal and the operation procedure of the kit. 10 ml of an LB liquid culture medium was prepared in a 30-ml test tube and was sterilized in an autoclave at 121° C. for 20 minutes. After adding ampicillin to the culture medium to make a final concentration of 100 µg/ml, one platinum loop of the MT-10822 strain was planted and cultured at 37° C. and 300 rpm for 20 hours. After fractionating 1 ml of the culture liquid to a suitable centrifugal tube, the fungus body was separated by centrifugal separation (15,000 rpm for 5 minutes). Subsequently, the plasmid DNA of pPT-DB1 was prepared from the fungus body by the alkali SDS extraction method.

Two kinds of PCR reactions were carried out by using 1 µg of the plasmid DNA of pPT-DB1 as a template. The PCR reaction No. 1 was carried out by repeating a procedure of 15 seconds of thermal denaturation (98° C.), 30 seconds of annealing (55° C.) and 120 seconds of elongation reaction (72° C.) by 25 cycles in a system of a total amount of 50 µl containing 50 pmol each of the primer described in the sequence number 1 of the sequence table and the M13 primer M4 (arrangement disclosed in the sequence number 2 in the sequence table) (the composition was in accordance with the conditions described in the kit). The PCR reaction No. 2 was carried out by conducting the same procedure as in the PCR reaction No. 1 in a system of a total amount of 50 µl containing 50 pmol each of the MUT4 primer (arrangement disclosed in the sequence number 3 sequence table) and the M13 primer RV (arrangement disclosed in the sequence number 4 in the sequence table) (the composition was in accordance with the conditions described in the kit). Analysis of DNA amplified products was carried out for 5 μl each of the reaction completed solutions of the PCR reactions No. 1 and No. 2 by agarose electrophoresis (agarose concentration: 1.0% by weight), and the presence of the DNA amplified product was confirmed. The excessive primers and the dNTP were removed from the respective PCR reaction completed solutions by using Microcon 100 (produced by Takara Shuzo Co., Ltd.), and then TE (trishydroxymethylaminomethane EDTA buffer solution) was added thereto to prepare 50 μl each of the solutions. Annealing solutions of a total amount of 47.5 μl containing 0.5 μl each of the TE solutions (the composition was in accordance with the conditions described in the kit) were prepared, and after carrying out a thermal denaturation treatment (98° C.) for 10 minutes, cooling was carried to 37° C. over 60 minutes at a constant rate, followed by maintaining at 37° C. for 15 minutes, so as to conduct the annealing treatment. 0.5 μl of TAKARALA Taq was added to the annealing treatment solution, which was subjected to a heat treatment at 72° C. for 3 minutes, so as to complete a heterodouble strand. 50 pmol each of the M13 primer M4 (arrangement disclosed in the sequence number 2 in the sequence table) and the M13 primer RV (arrangement disclosed in the sequence number 4 in the sequence table) were added to make a total amount of 50 μl, and then the PCR reaction No. 3 was carried out by repeating a procedure of 15 seconds of thermal denaturation (98° C.), 30 seconds of annealing (55° C.) and 120 seconds of elongation reaction (72° C.) by 25 cycles. Analysis of DNA amplified products was carried out for 5 μl of the reaction completed solutions of the PCR reaction No. 3 by agarose electrophoresis (using low melting point agarose Type VII produced by Sigma Aldrich Japan, Inc., agarose concentration: 0.8 by weight), and the presence of about 2.0 Kbp of the DNA amplified product was confirmed. Subsequently, only a DNA fragment of about 2.0 Kbp was cut out from the agarose gel, and after finely pulverizing the agarose fragment (about 0.1 g), which was suspended in 1 ml of the TE solution, it was kept at 55° C. for 1 hour to completely melt the agarose. Phenol/chloroform extraction and ethanol precipitation were carried out for the molten solution in ordinary procedures to purify the DNA fragment, and it was finally dissolved in 10 μl of TE. After cutting about 2.0 kbp of the purified DNA fragment by the restriction enzymes EcoRI and HindIII, phenol/chloroform extraction and ethanol precipitation were carried out for the restriction enzyme treated solution to purify the DNA fragment, and it was finally dissolved in 10 μl of TE. Similarly, the pPT-DB1 was cut by EcoRI and HindIII as the sole restriction enzyme site on the pPT-DB1, and agarose electrophoresis was carried out (using low melting point agarose Type VII produced by Sigma Aldrich Japan, Inc., agarose concentration: 0.7 by weight), so as to cut out only about 2.7 Kbp of the DNA fragment from the agarose gel. After the agarose fragment (about 0.1 g) thus cut out was finely pulverized and suspended in the TE solution, it was maintained at 55° C. for 1 hour to completely melt the agarose. Phenol/chloroform extraction and ethanol precipitation were carried out for the molten solution to purify the DNA fragment, and it was finally dissolved in 10 μl of TE. The amplified DNA product thus obtained and the pPT-DB1 fragment were ligated by using a DNA ligation kit (produced by Takara Shuzo Co., Ltd.), and then competent cells of Escherichia coli HB101 (produced by Toyobo Co., Ltd.) was transformed to prepare an Escherichia coli bank.

10 mL of an LB culture medium containing 40 μg/ml of ferric sulfate heptahydrate and 10 μg/ml of cobalt chloride dihydrate (hereinafter, referred to as an activity expression culture medium) was prepared in a 30-ml test tube and sterilized by an autoclave at 121° C. for 20 minutes. After adding ampicillin to the culture medium to make a final concentration of 100 μg/ml, one platinum loop each of five clones arbitrarily selected from the Escherichia coli bank was planted and cultured at 37° C. and 300 rpm for about 20 hours. After fractionating 1 ml of the culture completed liquid to a suitable centrifugal tube, the fungus body was separated by centrifugal separation (15,000 rpm for 5 minutes). The fungus body was suspended in 200 μl of a potassium phosphate buffer solution (pH 7.0), and 1% by weight of acrylonitrile was added thereto, followed by reacting at 10° C. for 2 minutes. The same amount as the reaction solution of a 1-M phosphoric acid aqueous solution was added to the reaction solution to terminate the reaction, and the concentration of acrylamide thus produced was measured by the similar HPLC analysis as Example 2. As a result, production of acrylamide was confirmed in four clones among the five clones, and thus it was confirmed that the nitrile hydratase activity was maintained.

Fungus bodies of the four clones were separated from 1 ml each of the reminders of the culture medium having been subjected to the measurement of the nitrile hydratase activity, and plasmid DNA of the respective clones was prepared by the alkali SDS extraction method. Subsequently, the base sequences of the nitrile hydratase structural genes of the respective clones were determined by the primer extension method using a sequencing kit and Autosequencer 373A produced by ABI Inc. As a result, in the clone No. 1 shown in Table 1, the sixth Leu on the α subunit of the nitrile hydratase was substituted by Met.

TABLE 1

| Clone NO. | Mutation point (in α subunit) | Change of amino acid sequence | | Change of base sequence | |
|---|---|---|---|---|---|
| | | Before substitution | After substitution | Before substitution | After substitution |
| No. 1 | α-sixth | Leu | Met | CTG | ATG |

Subsequently, in order to substitute the 126th Phe on the α subunit by Tyr, a site-specific mutational introduction was carried out by using the plasmid DNA of the clone No. 1 as a template in the same procedures as in the foregoing. That is, 10 ml of an LB liquid culture medium was prepared in a 30-ml test tube and was sterilized in an autoclave at 121° C. for 20 minutes. After adding ampicillin to the culture medium to make a final concentration of 100 μg/ml, one platinum loop of the clone No. 1 strain was planted and cultured at 37° C. and 300 rpm for about 20 hours. After fractionating 1 ml of the culture liquid to a suitable centrifugal tube, the fungus body was separated by centrifugal separation (15,000 rpm for 5 minutes). Subsequently, the plasmid DNA of the clone No. 1 was prepared from the fungus body by the alkali SDS extraction method.

Two kinds of PCR reactions were carried out by using 1 μg of the plasmid DNA of the clone No. 1 strain as a template. The PCR reaction No. 4 was carried out by repeating a procedure of 15 seconds of thermal denaturation (98° C.), 30 seconds of annealing (55° C.) and 120 seconds of elongation reaction (72° C.) by 25 cycles in a system of a total amount of 50 μl containing 50 pmol each of the primer described in the sequence number 5 of the sequence table and the M13 primer M4 (arrangement disclosed in the sequence number 2 in the sequence table) (the composition was in accordance with the conditions described in the kit). The PCR reaction No. 5 was carried out by conducting the same procedure as in the PCR reaction No. 4 in a system of a total amount of 50 μl containing 50 pmol each of the MUT4 primer (arrangement disclosed in the sequence number 3 in the sequence table) (the composition was in accordance with the conditions described in the kit) and the M13 primer RV (arrangement disclosed in the sequence number 4 in the sequence table). Analysis of DNA amplified products was carried out for 5 μl each of the reaction completed solutions of the PCR reactions No. 4 and No. 5 by agarose electrophoresis (agarose concentration: 1.0% by weight), and the presence of the DNA amplified product was confirmed. An *Escherichia coli* bank was prepared in the same manner as in the case of the clone No. 1.

One platinum loop each of five clones arbitrarily selected from the *Escherichia coli* bank was planted in 10 ml of the same activation expression culture medium as in the case of the clone No. 1 and cultured at 37° C. and 300 rpm for about 20 hours. After fractionating 1 ml of the culture liquid to a suitable centrifugal tube, the nitrile hydratase activity was measured. As a result, production of acrylamide was confirmed in four clones among the five clones, and thus it was confirmed that the nitrile hydratase activity was maintained.

Fungus bodies of the four clones were separated from 1 ml each of the reminders of the culture medium having been subjected to the measurement of the nitrile hydratase activity, plasmid DNA of the respective clones was prepared by the alkali SDS extraction method. Subsequently, the base sequences of the nitrile hydratase structural genes of the respective clones were determined by the same procedures as in the case of the clone No. 1. As a result, in the clone No. 2 shown in Table 2, the sixth Leu on the α subunit of the nitrile hydratase was substituted by Met, and the 126th Phe on the α subunit was substituted by Tyr.

TABLE 2

| Clone NO. | Mutation point (in α subunit) | Change of amino acid sequence | | Change of base sequence | |
|---|---|---|---|---|---|
| | | Wild type | Mutant | Wild type | Mutant |
| No. 2 | α-sixth | Leu | Met | CTG | ATG |
| | α-126th | Phe | Tyr | TTC | TAC |

Subsequently, in order to substitute the 212th Ser on the β subunit by Tyr, a site-specific mutational introduction was carried out by using the plasmid DNA of the clone No. 2 as a template in the same procedures as in the foregoing.

That is, 10 ml of an LB liquid culture medium was prepared in a 30-ml test tube and was sterilized in an autoclave at 121° C. for 20 minutes. After adding ampicillin to the culture medium to make a final concentration of 100 μg/ml, one platinum loop of the clone No. 2 strain was planted and cultured at 37° C. and 300 rpm for about 20 hours. After fractionating 1 ml of the culture liquid to a suitable centrifugal tube, the fungus body was separated by centrifugal separation (15,000 rpm for 5 minutes). Subsequently, the plasmid DNA of the clone No. 1 was prepared from the fungus body by the alkali SDS extraction method.

Two kinds of PCR reactions were carried out by using 1 μg of the plasmid DNA of the clone No. 2 strain as a template. The PCR reaction No. 6 was carried out by repeating a procedure of 15 seconds of thermal denaturation (98° C.), 30 seconds of annealing (55° C.) and 120 seconds of elongation reaction (72° C.) by 25 cycles in a system of a total amount of 50 μl containing 50 pmol each of the primer described in the sequence number 6 of the sequence table and the M13 primer M4 (arrangement disclosed in the sequence number 2 in the sequence table) (the composition was in accordance with the conditions described in the kit). The PCR reaction No. 7 was carried out by conducting the same procedure as in the PCR reaction No. 6 in a system of a total amount of 50 μl containing 50 pmol each of the MUT4 primer (arrangement disclosed in the sequence number 3 in the sequence table) and the M13 primer RV (arrangement disclosed in the sequence number 4 in the sequence table) (the composition was in accordance with the conditions described in the kit). Analysis of DNA amplified products was carried out for 5 μl each of the reaction completed solutions of the PCR reactions No. 6 and No. 7 by agarose electrophoresis (agarose concentration: 1.0% by weight), and the presence of the DNA amplified product was confirmed. An *Escherichia coli* bank was prepared in the same manner as in the case of the clone No. 1.

One platinum loop each of five clones arbitrarily selected from the *Escherichia coli* bank was planted in 10 ml of the same activation expression culture medium as in the case of the clone No. 1 and cultured at 37° C. and 300 rpm for about 20 hours. After fractionating 1 ml of the culture liquid to a suitable centrifugal tube, the nitrile hydratase activity was measured. As a result, production of acrylamide was confirmed in four clones among the five clones, and thus it was confirmed that the nitrile hydratase activity was maintained.

Fungus bodies of the four clones were separated from 1 ml each of the reminders of the culture medium having been subjected to the measurement of the nitrile hydratase activity, plasmid DNA of the respective clones was prepared by the alkali SDS extraction method. Subsequently, the base sequences of the nitrile hydratase structural genes of the respective clones were determined by the same procedures as in the case of the clone No. 1. As a result, in the clone No. 3 shown in Table 3, the 212th Ser on the β subunit was substituted by Tyr.

TABLE 3

| Clone NO. | Mutation point | Change of amino acid sequence | | Change of base sequence | |
|---|---|---|---|---|---|
| | | Wild type | Mutant | Wild type | Mutant |
| No. 3 | α-sixth | Leu | Met | CTG | ATG |
| | α-126th | Phe | Tyr | TTC | TAC |
| | β-212th | Ser | Tyr | TCC | TAC |

The fungus body of the clone No. 3 was cultured to obtain a fungus body required for the reaction. A typical culture example will be shown below.

100 ml of a culture medium of the following composition was prepared in a 500-ml Erlenmeyer flask with a baffle and was sterilized in an autoclave at 121° C. for 20 minutes. After adding ampicillin to the culture medium to make a final concentration of 50 μg/ml, one platinum loop of the fungus body of the clone No. 3 was planted and cultured at 37° C. and 130 rpm for 20 hours. Only the fungus body was separated from the culture liquid by centrifugal separation (15,000 G for 15 minutes), and after again suspending the fungus body in 50 ml of physiological saline, a wet fungus body is obtained by again conducting centrifugal separation.

| Culture Medium Composition | |
|---|---|
| Yeast extract | 5.0 g/L |
| Polypepton | 10.0 g/L |
| NaCl | 5.0 g/L |
| Cobalt chloride hexahydrate | 10.0 mg/L |
| Ferric sulfate heptahydrate | 40.0 mg/L |
| | pH 7.5 |

(2) Synthesis Reaction of Acrylamide by Hydration of Acrylonitrile 2 parts by weight of the wet fungus body obtained in the foregoing culture process was suspended in 98 parts by weight of a 0.3 mM-NaOH aqueous solution, and the suspension and acrylonitrile were continuously fed at 50 g/h and 30 g/h, respectively, to a 1-L glass flask as the first reactor having 400 g of water charged under stirring, while the reaction solution was continuously withdrawn at 80 g/h to maintain the liquid level at a constant level. The solution was then continuously fed to 20 m of a Teflon tube having an inner diameter of 5 mm as the second reactor. The reaction temperatures were controlled in such a manner that the first reactor and the second reactor were immersed in a water bath at about from 10 to 20° C. to control the inner liquid temperature to 15° C.

As a result of analysis of the reaction solution at the outlet of the second reactor by HPLC analysis after 200 hours from the start of the reaction, only acrylamide was present in the reaction solution (concentration: 50% by weight), and acrylonitrile was below the detection limit (100 ppm by weight).

Comparative Example 1

The procedures were carried out in such a manner that only the agitation vessel as the first reactor was used as a reactor, while the reaction time was the same as in Example. That is, the same procedures as in Example were carried out except that the reactor was changed to a 2-L glass flask, and the amount of liquid inside it was changed to 800 g.

As a result of analysis of the reaction solution at the outlet of the reactor by HPLC analysis after 200 hours from the start of the reaction, 48% by weight acrylamide and 1.9% by weight of acrylonitrile were detected in the reaction solution. Consequently, it was confirmed that the unreacted acrylonitrile remained in this Comparative Example, and the reaction was incomplete.

Comparative Example 2

The same procedures as in Example 1 were carried out except that the reaction solution at the outlet of the first reactor was continuously fed to a 1-L glass flask as the first reactor having 400 g of water charged as similar to the first reactor under stirring, while the reaction solution was continuously withdrawn to maintain the liquid level at a constant level.

As a result of analysis of the reaction solution at the outlet of the second reactor by HPLC analysis after 200 hours from the start of the reaction, 49.5% by weight acrylamide and 3,000 ppm by weight of acrylonitrile were detected in the reaction solution. It was also confirmed that the unreacted acrylonitrile remained in this Comparative Example, and the reaction was incomplete.

Effect of the Invention

According to the invention, an amide compound aqueous solution of a high concentration can be produced by hydrating a nitrile compound at a high conversion rate, in which no residual nitrile compound is observed, and the production can be easily carried out in a relatively short period of time, and therefore, the process of the invention can be suitably employed as an industrial production process of an amide compound.

What is claimed is:

1. A process for continuously producing an amide compound, comprising reacting a microorganism fungus body containing nitrile hydratase or a processed product of the microorganism fungus body with a nitrile compound in an aqueous medium in a preceding reactor comprising a suspended bed, and subjecting a reaction solution thus obtained to reaction in a subsequent reactor under conditions having a plug flow region, wherein the reaction time in the preceding reactor is from 20% to 99% of the total reaction time, and the reaction time in the subsequent reactor is from 1% to 80% of the total reaction time.

2. A production process according to claim 1, wherein said nitrile compound is acrylonitrile, and a ratio of water and acrylonitrile upon contacting with said fungus body or said processed product of said fungus body is from 0.4 to 1.5 parts by weight of acrylonitrile per 1.0 part by weight of water.

3. A production process according to claim 2, wherein said microorganism fungus body is a transformant obtained by expressing a nitrile hydratase gene cloned from said microorganism in an arbitrary host.

4. A production process according to claim 1, wherein said microorganism fungus body is a transformant obtained by expressing a nitrile hydratase gene cloned from said microorganism in an arbitrary host.

* * * * *